(12) United States Patent
Murata et al.

(10) Patent No.: US 9,044,166 B2
(45) Date of Patent: Jun. 2, 2015

(54) OPTICAL TOMOGRAPHIC IMAGE PHOTOGRAPHING APPARATUS

(75) Inventors: Toshio Murata, Milpitas, CA (US); Yukihiro Higuchi, Toyota (JP)

(73) Assignee: NIDEK CO., LTD., Aichi (JP)

( * ) Notice: Subject to any disclaimer, the term of this patent is extended or adjusted under 35 U.S.C. 154(b) by 343 days.

(21) Appl. No.: 13/448,738

(22) Filed: Apr. 17, 2012

(65) Prior Publication Data

US 2012/0281235 A1    Nov. 8, 2012

(30) Foreign Application Priority Data

Apr. 18, 2011  (JP) .................................. 2011-091720

(51) Int. Cl.
*G01B 9/02* (2006.01)
*A61B 3/10* (2006.01)
*G01N 21/47* (2006.01)

(52) U.S. Cl.
CPC ............ *A61B 3/102* (2013.01); *G01N 21/4795* (2013.01)

(58) Field of Classification Search
CPC ........... G01B 9/02083; G01B 9/02087; G01B 9/02091; A61B 3/102
USPC ................................................. 356/479, 497
See application file for complete search history.

(56) References Cited

U.S. PATENT DOCUMENTS

| 6,980,299 | B1 | 12/2005 | De Boer |
| 7,527,378 | B2 | 5/2009 | Fukuma et al. |
| 7,880,895 | B2 | 2/2011 | Yamada et al. |
| 7,954,946 | B2 | 6/2011 | Murata |
| 8,018,598 | B2 | 9/2011 | Cense et al. |
| 2010/0014089 | A1* | 1/2010 | Yamada et al. ............... 356/450 |

FOREIGN PATENT DOCUMENTS

| JP | A-2007-215733 | 8/2007 |
| JP | A-2008-501118 | 1/2008 |
| JP | A-2008-029467 | 2/2008 |
| JP | A-2010-012111 | 1/2010 |
| JP | A-2010-029648 | 2/2010 |

* cited by examiner

*Primary Examiner* — Tarifur Chowdhury
*Assistant Examiner* — Jonathon Cook
(74) *Attorney, Agent, or Firm* — Oliff PLC

(57) ABSTRACT

An optical tomographic image photographing apparatus includes: an OCT optical system for capturing tomographic images of an object to be examined, the OCT optical system including a light source, a splitter for splitting a light from the light source into a measurement optical path and a reference optical path, an optical scanner, and a detector for detecting a spectrum of light obtained by combining the light of the measurement optical path reflected from the object and the light from the reference optical path; a drive unit to move at least a part of optical components of the OCT optical system in an optical axial direction; a monitor to output at least the tomographic image; and a display controller for displaying the tomographic image and identifying information used to determine whether the tomographic image output to the monitor is a normal image or a reverse image.

14 Claims, 5 Drawing Sheets

Retinal

Choroidal

OPTICAL TOMOGRAPHIC IMAGE PHOTOGRAPHING APPARATUS

CROSS-REFERENCE TO RELATED APPLICATIONS

This application is based upon and claims the benefit of priority from the prior Japanese Patent Application No. 2011-091720, filed April 18, the entire contents of which are incorporated herein by reference.

BACKGROUND

1. Technical Field

The present invention relates to an optical tomographic image photographing apparatus used to capture tomographic images of an object to be examined.

2. Related Art

An apparatus conventionally used to capture tomographic images of an object to be examined is an optical coherence tomography (OCT) device.

A known example of the optical coherence tomography device is a Fourier domain OCT device which captures tomographic images of an object to be examined through Fourier analysis of spectral information obtained by a light receiving element (see the Patent Document 1). As Fourier domain OCT devices, there are known SD-OCT where a spectroscopic optical system is provided in a light reception system, and SS-OCT where a wavelength-variable light source is provided in a light projection system.

A tomographic image obtained by an interference optical system based on the principle of Fourier domain OCT has an utmost photographic sensitivity (interference sensitivity) at a depth position where a measurement light and a reference light have an equal optical path length. The photographic sensitivity is more weakened with an increasing distance from the depth position. Therefore, a part of the image obtained near the depth position has a high photographic sensitivity and a high resolution, whereas other parts of the image obtained away from the depth position fail to have expected levels of sensitivity and resolution.

The apparatuses disclosed in the Patent Documents 1 and 2 are adapted to set different modes (retinal mode and choroidal mode); one mode is to output a tomographic image captured when fundus is located behind the depth position where the optical path lengths of the measurement and reference lights become equal (normal image), while the other mode is to output a tomographic image captured when fundus is located ahead of the depth position where the optical path lengths of the measurement and reference lights become equal (reverse image).

RELATED ART DOCUMENTS

Patent Documents

Patent Document 1: JP 2010-29648A
Patent Document 2: JP 2007-215733A

SUMMARY

In the event of any changes in a positional relationship between an object to be examined and the apparatuses disclosed in the Patent Documents 1 and 2 owing to some factors (for example, a large motion of the examinee's eye, unintentional displacement of the apparatus by an examiner), these apparatuses may display tomographic images different to the tomographic images initially obtained. In the case where the eye moves while these apparatuses are operating in the retinal mode, for example, a tomographic image where the sensitivity is high on the choroidal side is possibly displayed although the apparatuses are supposed to display a tomographic image in retinal mode.

The present invention has one purpose to provide an optical tomographic image photographing apparatus enabling appropriate observation of desired tomographic images.

Means of Solving the Problems

To achieve the above object, one aspect of the invention provides an optical tomographic image photographing apparatus, including: an optical coherence tomography (OCT) optical system for capturing tomographic images of an object to be examined, the OCT optical system including: a light source; a splitter for splitting a light from the light source into a measurement optical path and a reference optical path; an optical scanner placed in the measurement optical path and for scanning light on the object to be examined; and a detector for detecting a spectrum of light obtained by combining the light of the measurement optical path reflected from the object and the light from the reference optical path; a drive unit placed to move at least a part of optical components provided in the OCT optical system in an optical axial direction to adjust a difference in optical path length between the measurement optical path and the reference optical path; a monitor placed to output at least the tomographic image; and a display controller for displaying, on the monitor alongside the tomographic image, identifying information used to determine whether the tomographic image output to the monitor is a normal image or a reverse image.

DETAILED DESCRIPTION

Figure 1:
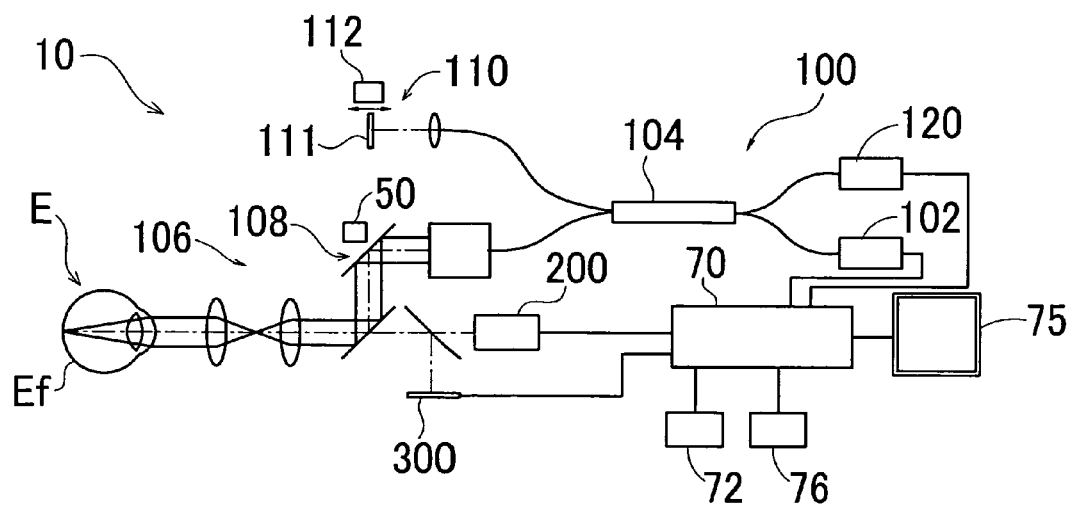
FIG. 1 is a schematic structural diagram to explain an optical tomographic image photographing apparatus of an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Hereinafter, a preferred embodiment of the present invention is described in detail referring to the drawings. FIG. 1 is a schematic structural diagram to explain an optical tomographic image photographing apparatus of the present embodiment. The apparatus described below is an ophthalmic photographing apparatus. In the description of the present embodiment, an axial direction, a horizontal direction, and a vertical direction of an examinee's eye (eye E) are respectively called Z direction, X direction, and Y direction. A direction along the surface of a fundus may be called as X-Y direction.

The configuration of the apparatus is briefly described. The apparatus is an optical coherence tomography device (OCT device) 10 used to photograph or capture tomographic images of a fundus Ef of the eye E. The OCT device 10 includes an interference optical system (OCT optical system) 100, a front observation optical system 200, a fixation target projecting unit 300, and a computing controller (CPU) 70.

The OCT optical system 100 irradiates a measurement light on the fundus. The OCT optical system 100 detects an interference state between the measurement light reflected from the fundus and a reference light by using a light receiving element (detector 120). The OCT optical system 100 has an irradiation position changing unit which changes an irradiation position of the measurement light on the fundus Ef (for example, optical scanner 108, fixation target projection unit 300) to change a photographing position on the fundus Ef. The controller 70 controls the operation of the irradiation position changing unit based on information of the photographing position set therein and obtains a tomographic image based on a light reception signal output from the detector 120.

<OCT Optical System>

The OCT optical system 100 is configured as an ophthalmic apparatus of optical coherence tomography. The OCT optical system 100 splits a light emitted from a light source 102 into a measurement light and a reference light by using a coupler (splitter) 104. The OCT optical system 100 guides the measurement light to the fundus Ef of the eye E by using a measurement optical system 106, while guiding the reference light to a reference optical system 110. Then, the OCT optical system 100 makes the detector (a light receiving element) 120 receive an interference light obtained by combining the measurement light reflected from the fundus Ef with the reference light.

The detector 120 detects an interference state between the measurement light and the reference light. According to the Fourier domain OCT, a spectral intensity of the interference light is detected by the detector 120, and data of the spectral intensity is subjected to Fourier transform to obtain a depth profile in a predetermined range. Examples of the Fourier domain OCT are Spectral-domain OCT (SD-OCT), and Swept-source OCT (SS-OCT).

According to the SD-OCT, a low coherence light source (a broadband light source) is used as the light source 102, and the detector 120 is provided with a spectral optical system (spectrometer) which spectrally divides the interference light into frequency components (wavelength components). The spectrometer includes, for example, a diffraction grating and a line sensor.

According to the SS-OCT, a wavelength scan light source (a wavelength-variable light source) which changes an outgoing wavelength periodically at short time intervals is used as the light source 102. The detector 120 is, for example, a single light receiving element. The light source 102 includes, for example, a light source, a fiber ring resonator, and a wavelength selective filter. Examples of the wavelength selective filter are combination of a diffraction grating and a polygonal mirror, and Fabry-Perot etalon device.

The light emitted from the light source 102 is split into the measurement light and the reference light by the coupler 104. The measurement light is transmitted through optical fibers and emitted into air, and the measurement light beam converges on the fundus Ef through the optical scanner 108 and other optical devices of the measurement optical system 106. The light reflected from the fundus Ef returns to the optical fibers by travelling through a similar optical path.

The optical scanner 108 makes the measurement light scan the fundus Ef in the X-Y direction (traverse direction). The optical scanner 108 is located at a position substantially conjugate with a pupil. The optical scanner 108 is, for example, two galvano mirrors whose light reflection angles are arbitrarily adjusted by a drive mechanism 50.

The light beam emitted from the light source 102 accordingly changes its reflection (travelling) direction. Then, the light beam is scanned on the fundus in any arbitrary directions, thereby changing the photographing position on the fundus Ef. Examples of the optical scanner 108 are a reflector mirror (a galvano mirror, a polygonal mirror, a resonant scanner), and an acousto-optic modulator (AOM) which changes a light travelling (deflection) direction.

The reference optical system 110 generates the reference light to be combined with a reflected light obtained when the measurement light is reflected from the fundus Ef. The reference optical system 110 may be of Michelson type or Mach-Zehnder type. The reference optical system 110 includes, for example, a reflection optical system (for example, reference mirror), wherein the light from the coupler 104 is reflected by the reflection optical system so that the light is transmitted back to the coupler 104 and then guided to the detector 120. Another example of the reference optical system 110 includes a transmission optical system (for example optical fibers), wherein the light from the coupler 104 is not transmitted back thereto but is directly guided to the detector 120.

For adjustment of a difference between the optical path lengths of the measurement light and the reference light, the apparatus moves at least a part of the optical components provided in the interference optical system 100 in an optical axial direction. For example, the reference optical system 110 moves the optical components in the optical path of the reference light (for example, a reference mirror 111) to adjust the difference between the optical path lengths of the measurement light and the reference light. For example, a drive mechanism 112 is driven to move the reference mirror 111 in the optical axial direction. A technical arrangement for changing the difference in the optical path length may be provided in the optical path of the measurement light of the measurement optical system 106. The optical components provided in the optical path of the measurement light (for example, an end portion of the optical fibers) are moved in the optical axial direction. A housing including the whole structure of the interference optical system 100 may be moved relative to the eye E to adjust the difference in the optical path length.

Figure 2A:
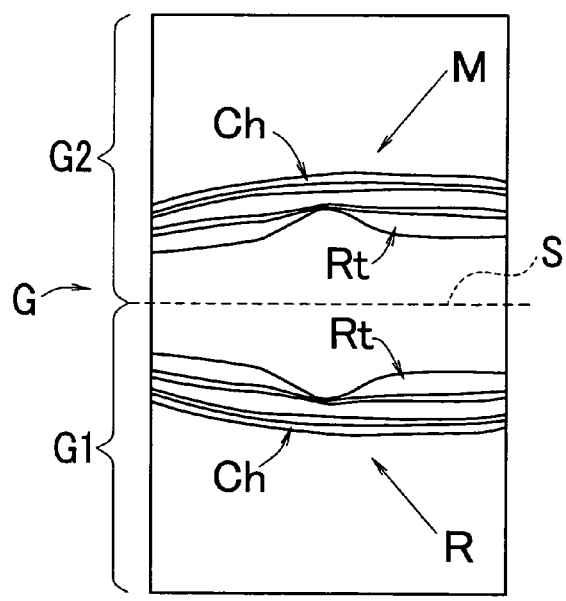
FIGS. 2A and 2B are diagrams showing examples of tomographic images obtained (formed) by an OCT optical system.
Figure 2B:
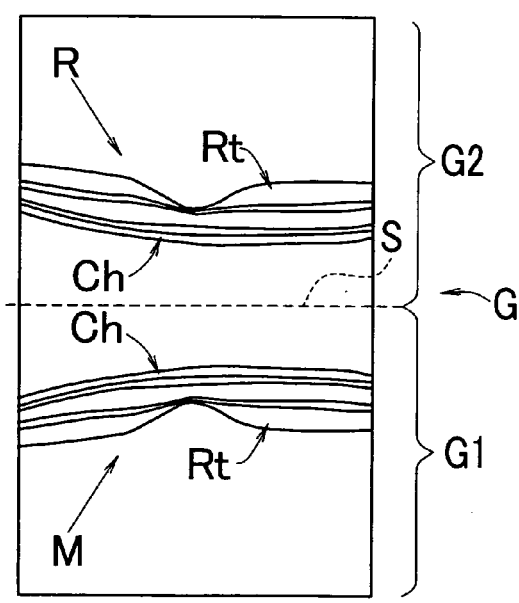

FIGS. 2A and 2B are diagrams respectively showing examples of a tomographic image obtained (formed) by the OCT optical system 200. A depth position S is a position corresponding to the optical path length of the reference light in a tomographic image G, where the optical path lengths of the measurement light and the reference light become equal.

The tomographic image G includes a first image region G1 behind the depth position S, and a second image region G2 ahead of the depth position S. The first image region G1 and the second image region G2 are symmetrical to each other with respect to the depth position S FIG. 2A is an example of the tomographic image when a normal image having a high photographic sensitivity on the retinal side is obtained. After the reference mirror 111 is positioned so that a retinal surface of the eye E is located behind the position where the optical path lengths of the measurement light and the reference light become equal, a fundus tomographic image (a normal image), where the sensitivity is higher on the side of a retinal surface Rt than on the side of choroid Ch, is obtained. The image has a better sensitivity on the retinal side because the retina is closer to the position where the optical path lengths are equal than the choroid.

In the given example, tomographic images formed in the first and second image regions are facing each other. A real image R is obtained in the first image region G1, and a mirror image M is obtained in the second image region G2.

FIG. 2B is an example of the tomographic image when a reverse image having a high photographic sensitivity on the choroidal side is obtained. When the reference mirror 111 is positioned so that a rear surface of the choroid is located ahead of the position where the optical path lengths of the measurement light and the reference light become equal, a fundus tomographic image (a reverse image) where the sensitivity is higher on the side of choroid Ch than on the side of retinal surface Rt. The image has a better sensitivity on the choroidal side because the choroid is closer to the position where the optical path lengths are equal than the retina.

In the given example, tomographic images formed in the first and second image regions G1 and G2 are opposite to each other. A real image R is obtained in the second image region G2, and a mirror image M is obtained in the first image region G1.

Describing how the image regions where the real image is obtained related to normal and reverse images, a normal image is obtained when the real image R is obtained in the first image region G1, whereas a reverse image is obtained when the real image R is obtained in the second image region G2. In other words, a normal image is obtained when the mirror image M is obtained in the second image region G2, whereas a reverse image is obtained when the mirror image M is obtained in the first image region G1.

The controller 70 extracts information of the image in the first image region G1 or the second image region G2 from the tomographic image G, and displays the extracted information on the screen of a monitor 75. The controller 70 may cut out the image region from the tomographic image G or may recreate the image from luminance-related information of the relevant image region.

Figure 3A:
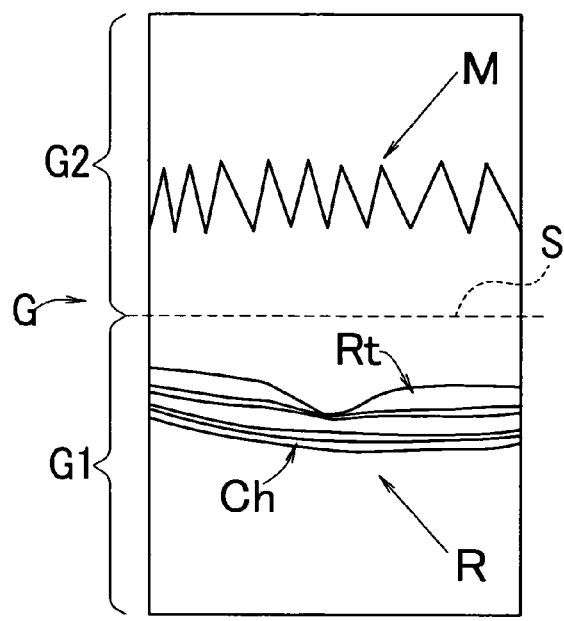
FIGS. 3A and 3B are diagrams showing examples of the tomographic images after a software-based dispersion correction is performed.
Figure 3B:
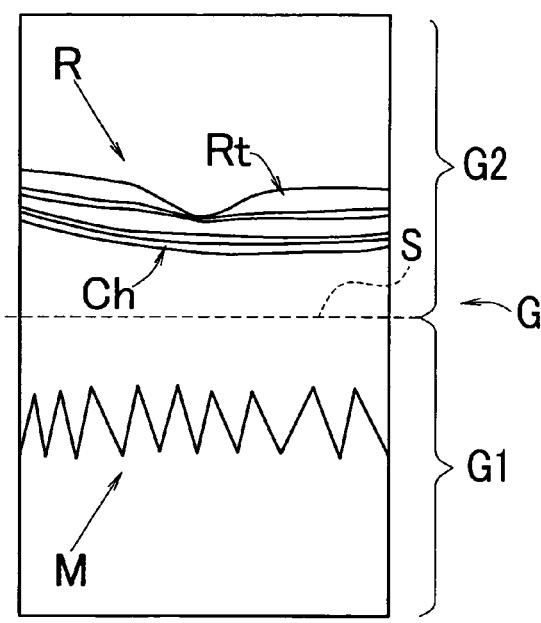

FIGS. 3A and 3B are diagrams respectively showing examples of the tomographic images after a software-based dispersion correction is performed. FIG. 3A illustrates an example when a normal image is obtained, and FIG. 3B illustrates an example when a reverse image is obtained. According to the present embodiment, the controller 70 performs the software-based dispersion correction to the spectral data output from the detector 120 and obtains a depth profile based on the dispersion-corrected spectral data. Because of that, real and mirror images respectively have different image qualities.

The controller 70 obtains the light spectral intensity based on a light reception signal output from the detector 120 and rewrites the obtained spectral intensity in the form of a function of wavelength $\lambda$. Then, the controller 70 transforms a spectral intensity $I(\lambda)$ into a function $I(k)$ for equally spaced wave number $k$ ($=2\pi/\lambda$).

Any adverse influence of dispersion mismatch between the measurement light and the reference light results in a phase shift of interference components, lower peaks of wavelength-combined signals, and broadening of signals (lower resolution). Therefore, the dispersion correction corrects the shifted phase back to an original phase per wavelength, thereby improving the deteriorated resolution associated with lowered interference signals. A phase shift $\phi(k)$, which is the function of the wave number k, is obtained beforehand, and any phase shift is corrected per k value based on $I(k)\cdot\exp\text{-}i\phi(k)$. The phase shift $\phi(k)$ subjected to the dispersion correction may be calculated in advance by calibration or the phase shift $\phi(k)$ may be calculated for the obtained tomographic image. A memory 72 stores therein parameters for dispersion correction (for example, phase shift $\phi(k)$). Then, the controller 70 performs Fourier transform to the spectral intensity $I(k)$ corrected by the dispersion correction data set therein to obtain information in a depth direction of the eye.

For example, a first dispersion correction value (for normal image), which is a dispersion correction value used to correct any dispersion-caused influences affecting a real image is obtained from the memory 72, the spectral data output from the detector 120 is corrected by means of the first dispersion correction value, and the corrected spectral intensity data is Fourier-transformed to form data of the tomographic image. The real image R thereby obtained has a high photographic sensitivity and a high resolution, whereas the mirror image M, which is corrected by means of the dispersion correction value for normal image, is obtained as a blurred image with a low resolution.

Therefore, a real image obtained in the first image region G1 has a high photographic sensitivity and a high resolution, whereas a mirror image obtained in the second image region G2, which is corrected by means of the dispersion correction value for normal image, is a blurred image with a low resolution (see FIG. 3A). On the other hand, when a real image is obtained in the second image region G2, a mirror image is obtained as a blurred image, which is corrected by means of the dispersion correction value for normal image, with a low resolution in the first image region G1 (see FIG. 3B).

The invention is not limited to the above. The software-based dispersion correction may be performed to the mirror image M, in which case the mirror image M is obtained as an image having a high photographic sensitivity and a high resolution, while the real image R is obtained as a blurred image with a low resolution.

For the detailed technique of the software-based dispersion correction, the following documents are available; U.S. Pat. No. 6,980,299, PCT Japanese Translation No. 2008-501118, and JP 2010-29648A.

<Front Observation Optical System>

The front observation optical system 200 is provided to obtain front images of the fundus Ef. The front observation optical system 200 includes an optical scanner which two-dimensionally scans the fundus using the measurement light emitted from the light source (for example, infrared light), and a second light receiving element which receives the reflected light from the fundus through a confocal aperture located at a position substantially conjugate with the fundus. The front observation optical system 200 is configured as a scan laser ophthalmoscope (SLO).

The observation optical system 200 may be configured as a fundus camera. The OCT optical system 100 may concurrently serve as the observation optical system 200, wherein data of tomographic images two-dimensionally obtained is used to obtain front images (for example, images integrated in the depth direction of three-dimensional tomographic images, integrated values of the spectrum data at X and Y positions).

<Fixation Target Projecting Unit>

The fixation target projecting unit 300 is provided with an optical system for guiding a visual axis direction of the eye E. The fixation target projecting unit 300 has a fixation target presented to the eye E to guide the eye E in a plurality of directions.

For example, the fixation target projecting unit 300 includes a visible light source which emits visible light. The fixation target projecting unit 300 two-dimensionally changes a position where the fixation target is presented to change the visual axis direction, thereby changing a site to be photographed. When the fixation target is presented in the same direction as a photographing optical axis, for example, a center portion of the fundus is set as the site to be photographed. When the fixation target is presented in an upper direction relative to the photographing optical axis, an upper portion of the fundus is set as the site to be photographed. Thus, the site to be photographed is changed depending on the position of the fixation target relative to the photographing optical axis.

The fixation target projecting unit 300 may adjust a fixation position by lighting one of LED lights arrayed in a matrix pattern or may scan light emitted from a light source using an optical scanner and adjust the fixation position by turning on and off the light source. The fixation target projecting unit 300 may be an internal fixation lamp device or an external fixation lamp.

<Controller>

The controller 70 is in charge of controlling the operations of the whole apparatus, such as the components of the systems 100 to 300. The controller 70 also serves as an image processor which processes obtained images and an image analyzer which analyzes obtained images. A CPU (Central Processing Unit) generally used constitutes the controller 70.

Figure 4A:
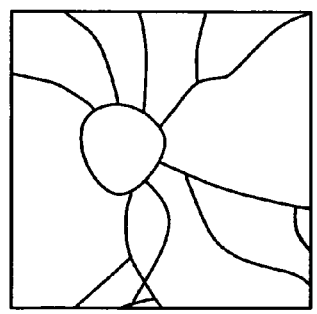
FIG. 4A is an example of a front image captured by a front observation optical system.
Figure 4B:
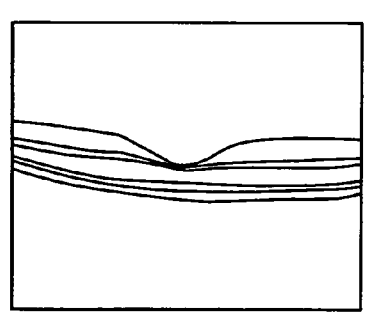
FIG. 4B is an example of a tomographic image captured by the OCT optical system.

FIG. 4A is an example of the front image captured by the front observation optical system 200. FIG. 4B is an example of the tomographic image captured by the OCT optical system 100. The controller 70 obtains, for example, the tomographic image (OCT image) through image processing based on a light reception signal output from the detector 120 of the OCT optical system 100. The controller 70 further obtains the front image based on a light reception signal output from the light receiving element of the front observation optical system 200. The controller 70 changes the fixation position by controlling the fixation target projecting unit 300.

The memory (a storage part) 72, a monitor 75, and a mouse (an operation input unit) 76 are electrically connected to the controller 70. The controller 70 controls a display screen of the monitor 75. The obtained fundus image is output as a still image or a moving image to the monitor 75 and also stored in the memory 72. In the memory 72 are recorded a variety of photographing-related information such as the obtained tomographic, front images, and photographing positions of the tomographic images. The controller 70 controls the components of the OCT optical system 100, front observation optical system 200, and fixation target projecting unit 300 based on operation signals output when an examiner manipulates the mouse 76. A more detailed configuration of the OCT device 10 is disclosed in JP 2008-29467A.

<Retinal Mode and Choroidal Mode>

Figure 5A:
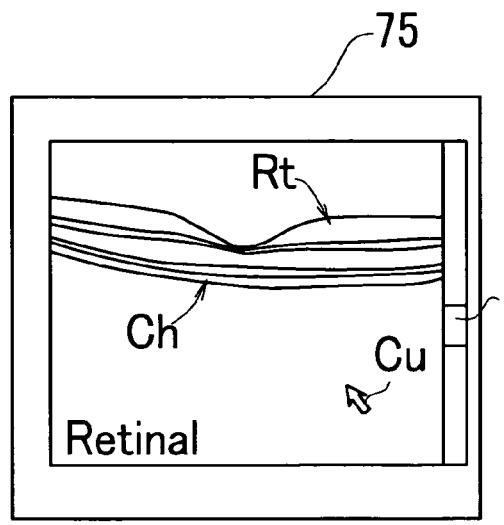
FIG. 5A is an example of an image display in a retinal mode on a monitor.
Figure 5B:
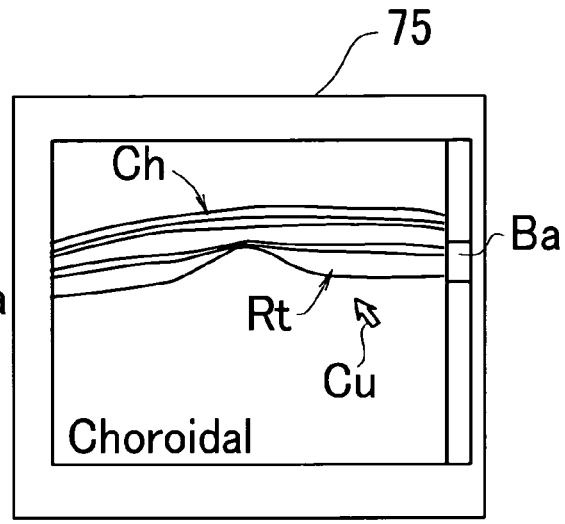
FIG. 5B is an example of an image display in a choroidal mode on the monitor.

The apparatus is adapted to set observation modes depending on a site to be observed so that any site to be observed by an examiner is observed with a high photographing sensitivity and a high resolution. FIG. 5A is an example of an image display in a retinal mode on the monitor 75, and FIG. 5B is an example of an image display in a choroidal mode on the monitor 75. The apparatus selects an observation mode between the retinal mode for displaying a retina portion with a high photographing sensitivity (a first mode for observing a front side of the fundus) and the choroidal mode for displaying a choroid-side portion with a high photographing sensitivity (a second mode for observing a rear side of the fundus of the examinee's eye).

The controller 70 has a first mode for outputting the obtained tomographic image as a first observation image (normal image) to the monitor (see FIG. 5A), and a second mode for outputting the obtained tomographic image as a second observation image (reverse image) to the monitor (see FIG. 5B), wherein the display state on the monitor 75 is changed when the observation mode is changed between the first and second observation modes based on image information and normal/reverse information of the obtained tomographic image.

To change the display state, the controller 70 changes a mode-identifying display for the examiner to identify whether the current mode is the first mode or the second mode (see FIGS. 5A and 5B).

The normal/reverse information teaches whether the obtained tomographic image is a normal image or a reverse image. The normal/reverse information can be provided in different patterns, for example, whether the obtained tomographic image is reversed, an image region where the tomographic image with a high resolution is obtained, and an image region where the tomographic image with a poor resolution is obtained. The controller 70 obtains the normal/reverse information based on a light reception signal output from the detector 120 (for example, tomographic image, and depth profile).

<Explanation of Operations>

Next, an example of the operation of the apparatus is explained in detail. After an examiner requests an examinee to gaze the fixation target, the examiner performs an alignment on the fundus. When a front image of the fundus is displayed on the monitor 75 as illustrated in FIG. 4A, the OCT image is obtained by the OCT optical system 100 based on a preset scanning pattern and displayed on the monitor 75.

<Adjustment of Difference in Optical Path Length>

The controller 70 drives the drive mechanism 112 based on a light reception signal output from the detector 120 to adjust a difference between the optical path lengths of the measurement light and the reference light so that the fundus tomographic image is obtained. The reference mirror 111 is moved in a predetermined moving distance suitable for an axial length of an examinee's eye, which is different from examinee to examinee. The retinal mode is set in an initial setting, and the controller 70 adjusts the optical path lengths so that a front image where the sensitivity is higher on the retinal side is obtained.

Figure 6:
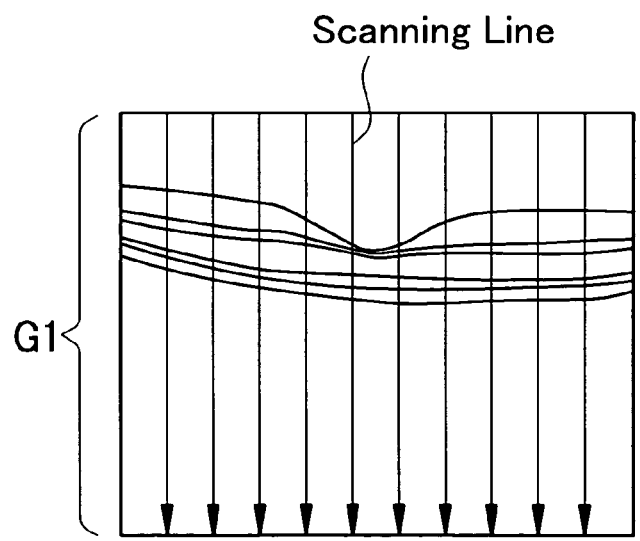
FIG. 6 is a diagram showing one example to set scanning lines.

The controller 70 moves the reference mirror 111 in predetermined steps suitable for a photographing range in the depth direction (for example, 2 mm). The controller 70 sets scanning lines in the depth direction on the images obtained at different positions to obtain a luminance distribution on each of the scanning lines (see FIG. 6).

The controller 70 analyzes the images obtained at the different positions and searches such a position of the reference mirror 111 that a real image is formed in the first image region G1. For example, the controller 70 identifies an image with a real-image luminance distribution (for example, luminance distribution with a sharp rise of luminance) formed in the first image region G1 through image processing (details of the technique are disclosed in JP 2010-12111A (U.S. Pat. No. 7,880,895)).

More specifically, it is determined that there is a real image in the first image region G1 in the case where the real-image luminance distribution is formed in half or more than half of the scanning lines in the first image region G1. Then, the controller 70 moves the reference mirror 111 from the position of the reference mirror 111 corresponding to the image identified as having a real image in the first image region G1 so that the real image R is displayed in a predetermined region of the monitor 75. Accordingly, the examiner is able to observe the front image of the fundus tomographic image on the monitor 75. After the automatic adjustment of the optical path lengths is completed, the controller 70 may continue the positional adjustment of the reference mirror 111 so that the fundus tomographic image is displayed in a predetermined region (optical path difference adjustment tracking).

<Display Change between Normal Image and Reverse Image>

Figure 7:
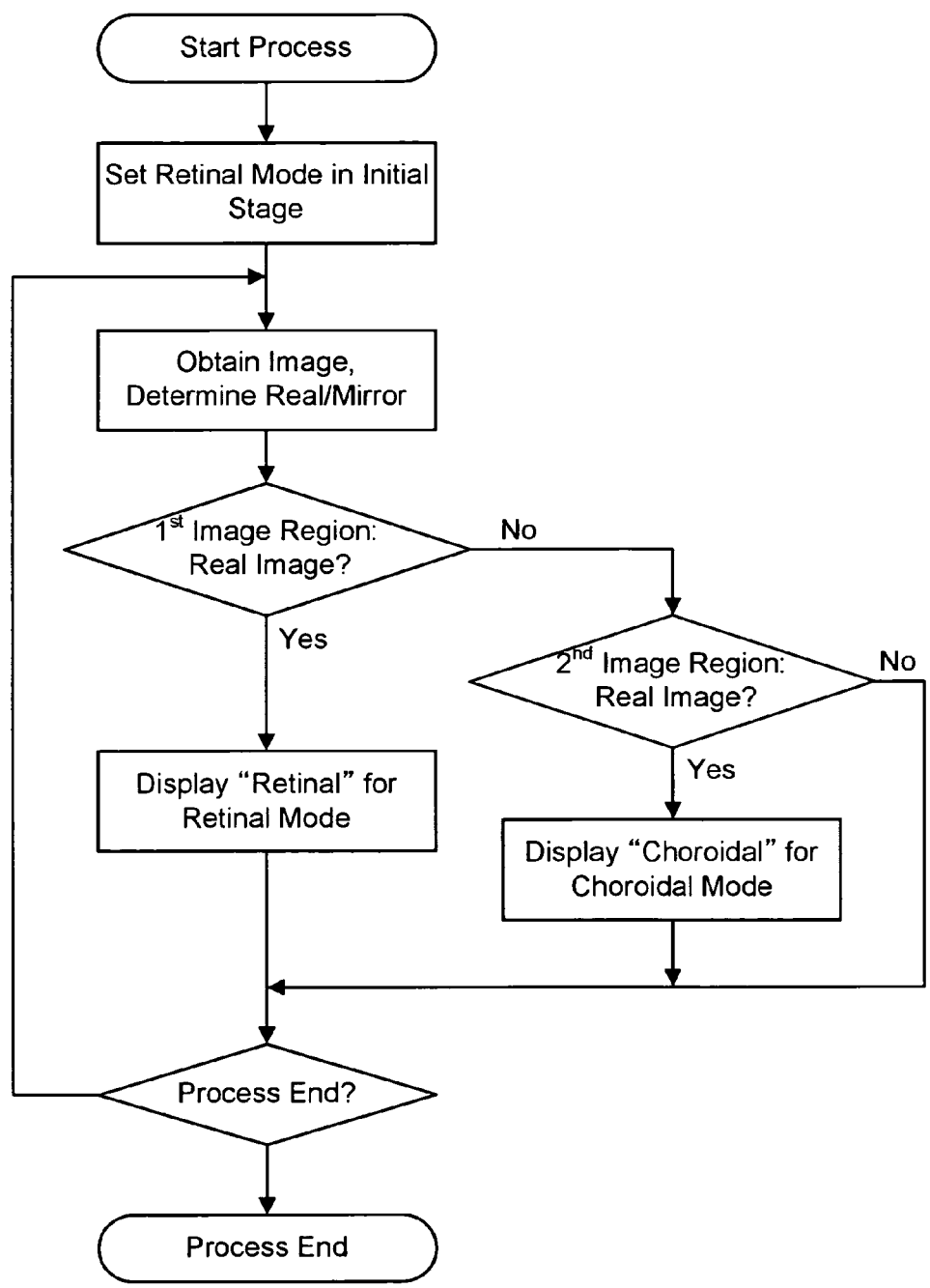
FIG. 7 is a flow chart showing an example of control of display change between a normal image and a reverse image.

FIG. 7 is a flow chart to showing an example of control of display change between a normal image and a reverse image. Of the first image region G1 and the second image region G2, the controller 70 selectively outputs the image region where the resolution of the tomographic image is higher to the monitor 75 based on the normal/reverse information of the obtained tomographic image.

In the following description, the controller 70 detects the display change between normal and reverse images of the tomographic image obtained in a predetermined image region, and accordingly changes the image region to be output to the monitor 75 (see FIGS. 2A, 2B, 3A, 3B, 5A, and 5B).

For example, the controller 70 identifies the image region where the real image of the obtained tomographic image is included to thereby obtain the normal/reverse information of the tomographic image. Then, the controller 70, based on the obtained normal/reverse information, extracts the image region including the high-resolution real image from the tomographic image G and outputs the extracted image region to the monitor 75. Thus, the controller 70 switches between the display in the retinal mode and the display in reverse image mode based on the obtained normal/reverse information. The controller 70 outputs the image region where the resolution is higher to the monitor 75 and displays the relevant mode.

<Retinal Mode>

In an initial stage, the observation mode is set to the retinal mode for outputting a normal image so that the image in the first image region G1 is extracted and displayed (a first display state). When a normal image is displayed on the monitor 75, the controller 70 displays a message indicating that the image displayed on the monitor 75 is a normal image (see FIG. 5A). For example, "Retinal" is displayed alongside the normal image because of a higher sensitivity on the retinal side. There are other ways of reporting the message, examples of which are graphic display (for example, icon), color display, and voice and/or sound.

Accordingly, the examiner is able to observe the fundus tomographic image on the monitor 75 knowing that the displayed image is a normal image. This is useful for identifying any lesion in the retinal region because the retinal-side image is displayed with a high sensitivity.

In the flow chart in FIG. 7, the controller 70 continues to obtain the tomographic image G until the photographing is terminated, and also obtains the normal/reverse information of each tomographic image G.

In a first determination process, the controller 70 determines whether a real image is obtained in the first image region G1, for example, determines whether an image corresponding to the real image is formed in the first image region G1. More specifically, the controller 70 determines whether there is a sharp rise of luminance in the first image region G1. The controller 70 may determine whether a luminance level/contrast in the first image region G1 (for example, a value obtained by subtracting a background image from a largest luminance value) is equal to or larger than a given value.

When the controller 70 determines in the first determination process that a real image is obtained in the first image region G1, the controller 70 determines that a normal image is obtained, leaving the retinal mode currently displayed on the monitor 75 unchanged (see FIG. 5A).

To observe the fundus tomographic image in in the choroidal mode, the examiner adjusts the difference between the optical path lengths of the measurement light and the reference light so that the choroid Ch is located ahead of the depth position S. For example, the examiner performs upward/downward movement of a display bar Ba, drag and drop of the tomographic image, and so on by using a cursor Cu. The controller 70 drives the drive mechanism 112 based on an operation signal output from the mouse 76 to move the reference mirror 111. As the reference mirror 111 moves, the real image R moves from its original position on the tomographic image G. To adjust the difference in optical path length, the examiner may move the housing in which the OCT optical system 100 is housed forward by manipulating a joystick not illustrated in the drawings.

After the difference in optical path length is adjusted, the formation of a real image shifts from the first image region G1 to the second image region G2. In the first determination process, it is determined that no real image is obtained in the first image region G1, and the controller 70 proceeds to a second determination process for determining whether a real image is obtained in the second image region G1.

In a second determination process, the controller 70 determines whether there is a sharp rise of luminance in the second image region G2. The controller 70 may determine whether a luminance level/contrast in the second image region G2 (for example, value obtained by subtracting a background image from a largest luminance value) is equal to or larger than a given value.

<Choroidal Mode>

When it is determined in the second determination process that a real image is obtained in the second image region G2, the controller 70 determines that a reverse image is obtained and switches the display mode on the monitor 75 to the choroidal mode (see FIG. 5B).

The controller 70 extracts the image of the second image region G2 and outputs the extracted image to the monitor 75. Then, a reverse image where the sensitivity is higher on the choroidal side is displayed on the monitor 75.

When the reverse image is displayed on the monitor 75, the controller 70 displays a message indicating that the image displayed on the monitor 75 is a reverse image (see FIG. 5B). For example, "Choroidal" is displayed alongside the reverse image because of a higher sensitivity on the choroidal side. There are other ways of reporting the message, examples of which are graphic display (for example, icon), color display, and voice and/or sound.

As a result, the examiner is able to observe the fundus tomographic image on the monitor 75 knowing that the image is a reverse image. This is useful for identifying any lesion in the choroidal region because the choroidal-side image is displayed with a high sensitivity.

As shown in FIG. 5B, the controller 70 may reverse the image in the second image region G2 from a display direction of the normal image to help the examiner discriminate the image from a normal image. For example, the controller 70 may display the tomographic image so that the retina is located above the choroid when a normal image is displayed, while displaying the tomographic image so that the retina is located below the choroid when a reverse image is displayed.

When the choroidal mode shifts to the retinal mode, the examiner preferably adjusts the difference in optical path length between the measurement light and the reference light so that the depth position S is located ahead of the fundus Ef.

<Storage of Tomographic Image>

As described so far, a scanning position/pattern desired by the examiner is set while the normal image or the reverse image is being displayed as a moving image, and a predetermined trigger signal is thereafter automatically or manually output. In response to the trigger signal thus output, the controller 70 controls the optical scanner 108 based on the set photographing conditions (for example, scanning position/pattern) and obtains a still image of the tomographic image meeting the photographing conditions based on an output signal of the detector 120. The controller 70 stores the obtained still image in the memory 72. The controller 70 may obtain a plurality of images at one scanning position to obtain an arithmetic addition mean image. In this case, the controller 70 preferably stores the normal/reverse information of the obtained tomographic image in association with the image information of the obtained tomographic image in the memory 72.

The controller 70 analyzes the tomographic image stored in the memory 72 through image processing and outputs an analysis result to the monitor 75. For example, the controller 70 measures a layer thickness distribution of fundus layers by image processing, and compares the layer thickness distribution of the eye E to a layer thickness distribution stored in a normal eye database. The controller 70 provides a mapping display of a measurement result of the layer thickness distribution. In this case, the controller 70 can perform various data analyses by utilizing the normal/reverse information stored in the memory 72. When the obtained tomographic image is a normal image, for example, analyzing processing for normal image focusing on retinal analysis is performed. When the obtained tomographic image is a reverse image, on the other hand, analyzing processing for reverse image focusing on choroidal analysis is performed.

As described so far, whether the tomographic image is a real image or a mirror image is detected, and the image region to be output to the monitor 75 is changed based on the position where the real image (or mirror image) is obtained, so that the observation in the retinal mode and the observation in in the choroidal mode are smoothly selected and performed in the event of unintentional motion of the eye E relative to the OCT optical system 100.

A possible misjudgment of the observation mode can be avoided by displaying identifying information to determine whether the tomographic image output to the monitor 75 is a normal image or a reverse image alongside the tomographic image based on the normal/reverse information of the tomographic image. For example, it is relatively easy to discriminate whether a tomographic image of yellow spots is a normal image or a reverse image when dents, which are specific to macula, are reversed. On the other hand, tomographic images of any other sites than the macula, having no such characteristic parts, may be difficult to determine whether they are normal images or reverse images even when the tomographic images are reversed. When the information is displayed as suggested, the observation mode can be easily known in any tomographic images.

<Real and Virtual Images Both Included in First Image Region G1 and Second Image Region G2>

When it is determined in the second determination process that no real image is obtained in the second image region G2, the controller 70 obtains the tomographic image again to determine whether the obtained tomographic image is a real image or a mirror image.

The controller 70 may determine whether real and mirror images are both present in one of the image regions (G1 or G2). The real and mirror images are present when the fundus Ef overlaps a position where the optical path lengths of the measurement light and the reference light become equal. In such a case, real and mirror images are both present in the first image region G1.

For example, when the image position of the fundus tomographic image is near the depth position S (for example, ¼ area of the first image region G1 from an upper end thereof), the controller 70 determines that real and mirror images are both present in one of the image regions.

The controller 70, which determined that real and mirror images are both present in one of the image regions, maintains the previous display state. In other words, the controller 70 does not update the previous display state but retains the display state according to the current observation mode.

In the case where the previous display corresponds to the retinal mode based on a determination result of whether the tomographic image is a real image or a mirror image, the display state corresponding to the retinal mode is retained (display of the first image region G1/display of "Retinal"). In the case where the tomographic image was previously displayed in in the choroidal mode, the display state in the choroidal mode is retained (display of the second image region G2/display of "Choroidal").

In the case where neither of a real image nor a mirror image is present in the tomographic image G (for example, when the eye is blinking), the controller 70 may continue the display state according to the current observation mode without updating the previous display state. For example, the controller 70 determines whether the tomographic image is present by the use of the luminance information of the tomographic image.

According to the processing steps described so far, too frequent changes of the displayed tomographic image and observation mode can be avoided even when the determination result for "real" or "virtual" keeps changing to and from "real", "virtual", "real+virtual", and "neither of real nor virtual".

In place of the processing steps described so far, the controller 70 may simply notify the examiner of "real+virtual". For example, the controller 70 displays "Retinal+Choroidal" alongside the tomographic image to notify that real and mirror images are both present.

Modified Embodiment

In the description given so far, the image region to be output to the monitor 75 is changed based on the normal/reverse information of the obtained tomographic image, however, the present invention is not necessarily limited thereto. For example, the dispersion correction data to be obtained from the memory 72 may be selected from a first dispersion correction data and a second dispersion correction data based on the normal/reverse information of the obtained tomographic image to output an observable tomographic image to the monitor. At the time, an image to be corrected by the software-based dispersion correction is changed depending on a real or mirror image.

In this case, for example, the first dispersion correction data for correcting dispersion to a real image (phase shift $\phi1(k)$) and the second dispersion correction data for correcting dispersion to a mirror image (phase shift $\phi2(k)$) are respectively calculated and stored in the memory 72.

Figure 8A:
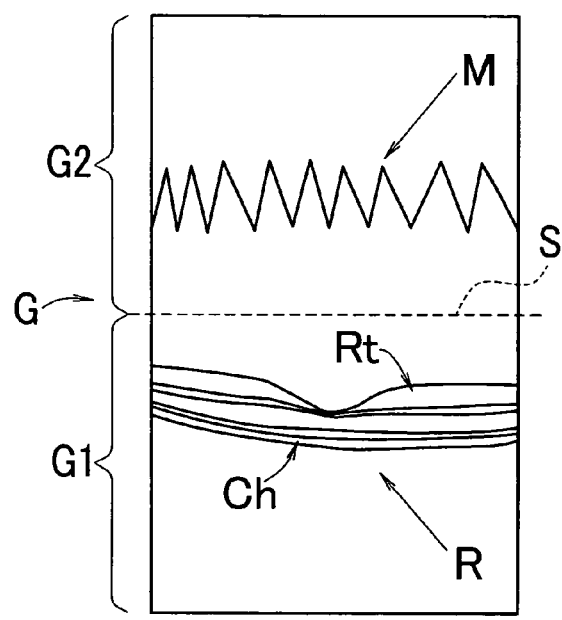
FIGS. 8A and 8B are diagrams showing examples where an image to be corrected through the software-based dispersion correction is changed between a real image and a mirror image.

In an initial setting, the controller 70, for example, corrects the spectral data using a first parameter for dispersion correction stored in the memory 72. As a result, the real image R in the first image region G1 is obtained as a clear image, and the mirror image M in the second image region G2 is obtained as a blurred image (see FIG. 8A). Then, the real image R in the first image region G1 is displayed on the monitor 75. At that time, it is determined that a real image is obtained in the first image region G1.

Figure 8B:
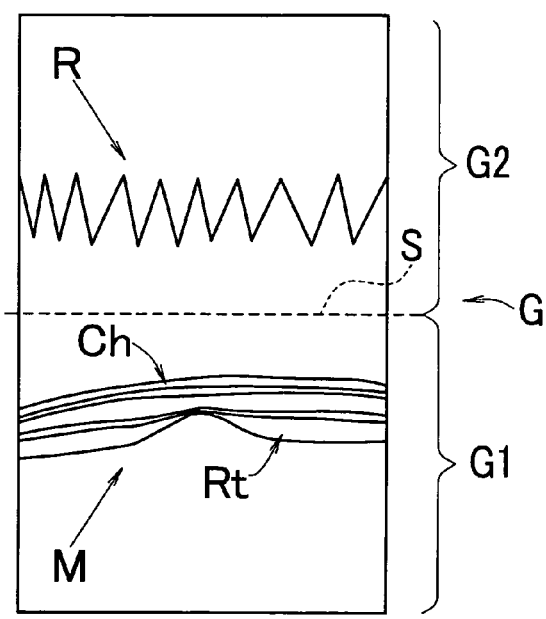

After that, the optical path lengths are adjusted so that the depth position S is located behind the choroid Ch. Then, the controller 70 detects that a real image is obtained in the second image region G2 based on an output signal of the detector 120, and corrects the spectral data using a second parameter for dispersion correction stored in the memory 72. As a result, the mirror image M in the first image region G1 is obtained as a clear image, and the real image R in the second image region G2 is obtained as a blurred image (see FIG. 8B). Then, the mirror image in the first image region G1 is displayed on the monitor 75.

When the choroidal mode shifts to the retinal mode, the examiner should adjust the difference between the optical path lengths of the measurement light and the reference light so that the depth position S is located ahead of the retina Rt. The controller 70 detects that a real image is obtained in the first image region G1 based on an output signal of the detector 120, and corrects dispersion of the real image using the first parameter for dispersion correction.

<Automatic Mode Change>

In the description given so far, the optical path lengths are adjusted depending on a degree of manipulation of the mouse 76, however, the present invention is not necessarily limited thereto. For example, a mode change switch is provided to switch between the retinal mode and the choroidal mode.

When a mode change signal for switching from the retinal mode to the choroidal mode is input, the controller 70 moves the reference mirror 111 in a direction where a reverse image is obtained. The controller 70, which determined that a real image is obtained in the second image region G2 based on an output signal of the detector 120, halts the movement of the reference mirror 111 and changes the display state from the current mode to the choroidal mode. The controller 70 may drive the drive mechanism 112 so that a real image is obtained in a predetermined area of the second image region G2.

When a mode change signal for switching from the choroidal mode to the retinal mode is input, the controller 70 moves the reference mirror 111 in a direction where a normal image is obtained. When the controller 70 determines that a real image is obtained in the first image region G1 based on an output signal of the detector 120, the controller 70 halts the movement of the reference mirror 111 and changes the current display state to the display state corresponding to the retinal mode. In this case, the controller 70 may drive the drive mechanism 112 so that a real image is obtained in a predetermined area of the first image region G1.

In determining whether the fundus tomographic image is a normal image or a reverse image, instead of the above technique, an image luminance distribution when a normal image is obtained and an image luminance distribution when a reverse image is obtained in one of the image regions may be compared to each other to set a determination criterion for determining whether "normal" or "reverse" based on a comparison result thereby obtained. An example of the criterion is whether a half-value width of a maximum luminance value is larger than a predetermined allowable width in one of the image regions.

In place of obtaining the normal/reverse information of the tomographic image using the luminance level of the tomographic image, the controller 70 may obtain information on whether the tomographic image in one of the image regions is reversed as the normal/reverse information of the obtained tomographic image and change the mode to be displayed. Irrespective of the first mode or second mode, the image information in one of the first image region G1 and the second image region G2 is output to the monitor.

The controller 70 detects whether the tomographic image obtained in the first image region G1 is reversed based on differences between shapes and forms of the tomographic image when a normal image is obtained and the tomographic image when a reverse image is obtained. More specifically, a portion of retinal pigment epithelium is extracted through image processing (for example, luminance value data exceeding a predetermined threshold corresponding to a luminance value of the retinal pigment epithelium is extracted), and whether the tomographic image is reversed is detected based on a curved shape of the portion of retinal pigment epithelium.

The layers of the fundus have different thicknesses and degrees of reflection. Utilizing the fact, information of the respective layers of the fundus may be detected through image processing to detect whether the image is reversed based on differences in the arrangement of layers between normal and reverse images. Whether the tomographic image is reversed may be detected based on the thicknesses of layers near the depth position where the optical path lengths of the measurement light and the reference light become equal. The thickness of a nerve fiber layer is used in the case of a normal image, while the thickness of a choroid is used in the case of a reverse image.

Other than the fundus photographing apparatus described so far, the present invention is applicable to any ophthalmic photographing apparatuses adapted to photograph predetermined sites of an examinee's eye. More specifically, the present invention is applicable to an eye anterior segment photographing apparatus used to capture tomographic images of an anterior segment of an examinee's eye.

The present invention is not just applicable to ophthalmic photographing apparatuses but is also applicable to optical tomographic image photographing apparatuses which capture tomographic images of body parts other than eyes (for example, skin, blood vessel) or non-biological samples. When the present invention is applied to optical tomographic image photographing apparatuses, a tomographic image where an examinee's surface side has a high photographic sensitivity is handled as a normal image, and a tomographic image where an examinee's back side has a high photographic sensitivity is handled as a reverse image.

The invention claimed is:
1. An optical tomographic image photographing apparatus, including:
   an optical coherence tomography (OCT) optical system that captures tomographic images of an object to be examined, the OCT optical system including:
      a light source;

a splitter that splits a light from the light source into a measurement optical path and a reference optical path;

an optical scanner, placed in the measurement optical path, that scans light on the object to be examined; and a detector that detects a spectrum of light obtained by combining the light of the measurement optical path reflected from the object and the light from the reference optical path;

a drive unit configured to move at least a part of optical components provided in the OCT optical system in an optical axial direction to adjust a difference in optical path length between the measurement optical path and the reference optical path;

a monitor configured to output at least the tomographic image; and a display controller that includes a processor and that is configured to determine, based on an output from the detector, identifying information identifying whether the tomographic image output to the monitor is a normal image or a reverse image, and to display the identifying information on the monitor alongside the tomographic image.

2. The optical tomographic image photographing apparatus according to claim 1, wherein the display controller determines whether the obtained tomographic image is a normal image or a reverse image based on image luminance distribution in the output from the detector and displays the identifying information on the monitor alongside the tomographic image based on a result of the determination.

3. The optical tomographic image photographing apparatus according to claim 1, wherein the display controller obtains normal/reverse information indicating whether the tomographic image is a normal image or a reverse image based on a light reception signal output from the detector, and the display controller displays the identifying information on the monitor alongside the tomographic image based on the obtained normal/reverse information.

4. The optical tomographic image photographing apparatus according to claim 1, wherein the display controller detects whether the tomographic image obtained in a predetermined image region changes to a normal image or a reverse image, and the display controller changes the image region to be output to the monitor in image information of the obtained tomographic image in response to the change.

5. The optical tomographic image photographing apparatus according to claim 1, wherein the display controller changes a display state on the monitor based on image information of the tomographic image and normal/reverse information indicating whether the tomographic image is a normal image or a reverse image.

6. The optical tomographic image photographing apparatus according to claim 1, wherein the display controller displays identifying information for an examiner to determine whether a current observation mode is a first observation mode or a second observation mode as the identifying information, the display controller performs Fourier analysis of spectral information obtained when a front surface of the object to be examined is located behind a depth position where optical path lengths of a measurement light and a reference light become equal to obtain the tomographic image of the object, and outputs the obtained tomographic image to the monitor as a first observation image in the first observation mode, and the display controller performs Fourier analysis of spectral information obtained when a rear surface of the object to be examined is located ahead of the depth position to obtain the tomographic image of the object, and outputs the obtained tomographic image to the monitor as a second observation image in the second observation mode.

7. The optical tomographic image photographing apparatus according to claim 6, wherein a display state on the monitor is changed when the current observation mode is changed between the first observation mode and the second observation mode based on image information and normal/reverse information of the tomographic image.

8. The optical tomographic image photographing apparatus according to claim 7, wherein the display controller changes a mode-identifying display for an examiner to determine whether the current observation mode is the first observation mode or the second observation mode to change the display state on the monitor.

9. The optical tomographic image photographing apparatus according to claim 6, wherein, of the image information of the obtained tomographic image, the display controller outputs image information of the tomographic image in one of a first image region located behind the depth position and a second image region located ahead of the depth position to the monitor regardless of whether the current observation mode is the first observation mode or the second observation mode, and the display controller determines whether the obtained tomographic image is a normal image or a reverse image and displays the identifying information based on a result of the determination.

10. The optical tomographic image photographing apparatus according to claim 1, further including an operation member to be operated by an examiner to drive the drive unit.

11. The optical tomographic image photographing apparatus according to claim 6, further including a memory for storing therein dispersion correction data for correcting dispersion in the tomographic image, wherein the display controller corrects the spectral information using the dispersion correction data obtained from the memory and performs Fourier analysis of the corrected spectral information to obtain the tomographic image of the object to be examined, the display controller determines whether the obtained tomographic image is a normal image or a reverse image, and according to image information of the obtained tomographic image, the display controller selectively outputs one of the first image region located behind the depth position and the second image region located ahead of the depth position, where the tomographic image has a higher resolution, to the monitor based on a result of the determination.

12. The optical tomographic image photographing apparatus according to claim 6, further including a memory for storing therein a first dispersion correction data for correcting dispersion to a real image of the tomographic image and a second dispersion correction data for correcting dispersion to a mirror image of the tomographic image, wherein the display controller corrects the spectral information using the dispersion correction data obtained from the memory and performs Fourier analysis of the corrected spectral information to obtain the tomographic image of the object to be examined, the display controller determines whether the obtained tomographic image is a normal image or a reverse image, the display controller outputs image information of the tomographic image in one of a first image region located behind the depth position and a second image region located ahead of the depth position to the monitor regardless of whether the current observation mode is the first observation mode or the second observation mode, and the dispersion correction data to be obtained from the memory is selected from the first dispersion correction data and the second dispersion correction data based on a result of the determination to output an observable tomographic image to the monitor.

13. The optical tomographic image photographing apparatus according to claim 1, wherein the OCT optical system is an OCT optical system for obtaining a tomographic image of a fundus of an examinee's eye.

14. The optical tomographic image photographing apparatus according to claim 13, further including:
a memory that stores therein normal/reverse information indicating whether the tomographic image is a normal image or a reverse image; and
an analyzer that analyzes the tomographic image through image processing,
wherein, the analyzer, using the normal/reverse information stored in the memory, performs analyzing processing for normal image focusing on retinal analysis when the obtained tomographic image is a normal image and performs analyzing processing for reverse image focusing on choroidal analysis when the obtained tomographic image is a reverse image.

* * * * *